(12) United States Patent
Kim (10) Patent No.: US 8,942,443 B2
(45) Date of Patent: Jan. 27, 2015

(54) COMPUTER SYSTEM AND COMPUTER-READABLE STORAGE MEDIUM FOR ART THERAPY

(75) Inventor: Seong-In Kim, Seoul (KR)

(73) Assignee: Korea University Industrial & Academic Collaboration Foundation, Seoul (KR)

(*) Notice: Subject to any disclaimer, the term of this patent is extended or adjusted under 35 U.S.C. 154(b) by 856 days.

(21) Appl. No.: 13/123,865

(22) PCT Filed: Oct. 30, 2009

(86) PCT No.: PCT/KR2009/006325
§ 371 (c)(1),
(2), (4) Date: Nov. 28, 2011

(87) PCT Pub. No.: WO2010/050767
PCT Pub. Date: May 6, 2010

(65) Prior Publication Data
US 2012/0063654 A1    Mar. 15, 2012

(30) Foreign Application Priority Data
Oct. 30, 2008  (KR) .................. 10-2008-0107289

(51) Int. Cl.
*G06K 9/00* (2006.01)
*G06Q 50/20* (2012.01)
(Continued)

(52) U.S. Cl.
CPC .............. *G06Q 50/20* (2013.01); *G06F 19/00* (2013.01); *G06F 19/345* (2013.01); *G06F 19/3481* (2013.01); *G06Q 50/22* (2013.01)
USPC .............................. 382/128; 434/236; 434/238

(58) Field of Classification Search
CPC ............... G06T 7/0012; G06T 2207/10116; G06T 2207/30004; G06T 7/0083; G06F 19/3418; G06F 19/322; G06F 7207/30072; G06F 19/321; G01N 15/1475; G09B 19/00; G09B 7/04; A61B 5/0002

USPC .......... 382/100, 128–132; 600/300, 301, 508, 600/523, 529, 549, 546, 547; 345/1.1, 2.2, 345/179; 434/236, 118, 170, 365; 705/2, 3, 705/5
See application file for complete search history.

(56) References Cited

U.S. PATENT DOCUMENTS 6,012,926 A * 1/2000 Hodges et al. .................. 434/236
6,102,846 A * 8/2000 Patton et al. ...................... 600/26
(Continued)

FOREIGN PATENT DOCUMENTS

KR   10-2004-0071820 A   8/2004
KR   10-2005-0093283 A   9/2005
(Continued)

OTHER PUBLICATIONS

[English Machine Translation pp. 1-16 (see IDS Nov. 28, 2011 line 1 Foreign Patent Publication)] Lee Chang Ju, Publication No. 00582987, Date of publication of specification: May 17, 2006, Apptication No. 1020050113046 filed Nov. 24, 2005.*
(Continued)

*Primary Examiner* — Hadi Akhavannik
*Assistant Examiner* — Medhi Rashidian
(74) *Attorney, Agent, or Firm* — Edwards Wildman Palmer LLP; Jeffrey D. Hsi (57) ABSTRACT

An art therapy computer system and a computer-readable storage medium having recorded a program for art therapy are disclosed. An aspect of the present invention provides a computer system that includes a drawing module, which presents a plurality of patterns and in which the drawing module selects a certain pattern, composes and colors a picture according to the working of a person tested for art therapy, an analysis module, which analyzes one or more factors from the colored picture, and a parsing module, which parses the psychological state, symptoms or disorders of the person tested for art therapy from the analyzed factors.

19 Claims, 8 Drawing Sheets

(51) Int. Cl.
*G06F 19/00* (2011.01)
*G06Q 50/22* (2012.01)
*G09B 19/00* (2006.01)

(56) References Cited

U.S. PATENT DOCUMENTS

| | | | |
|---|---|---|---|
| 6,648,649 B2* | 11/2003 | Rappaport | 434/236 |
| 6,896,655 B2* | 5/2005 | Patton et al. | 600/300 |
| 2004/0024287 A1* | 2/2004 | Patton et al. | 600/27 |
| 2005/0124851 A1* | 6/2005 | Patton et al. | 600/26 |
| 2011/0118555 A1* | 5/2011 | Dhumne et al. | 600/300 |
| 2011/0245633 A1* | 10/2011 | Goldberg et al. | 600/301 |

FOREIGN PATENT DOCUMENTS

| | | | |
|---|---|---|---|
| KR | 10-0582987 B1 | 5/2006 |
| KR | 10-0750871 B1 | 8/2007 |

OTHER PUBLICATIONS

International Search Report for International Application No. PCT/KR2009/006325 (Jun. 17, 2010).

Written Opinion of the International Searching Authority for the International Applicaton No. PCT/KR2009/006325 (Jun. 17, 2010).

* cited by examiner

CATS_KFD  questionnaire 2

1. Select your most favorite color and your least varorite color.

(1) What is your most favorite color?
   (2) What is your least favorite color?

2. Select your most favorite color in the primary colors, secondary colors and gray scales.

(1) What is your most favorite primary color?
   (2) What is your most favorite secondary color?
   (3) What is your most favorite gray scale?

3. Select the facial expression that matches your current state of mind.

very happy   very   so-so   unhappy   very unhappy

4. What is the color if you, your father and your mother are expressed in color?

(1) What is your color?
   (2) What is your father's color?
   (3) What is your mother's color?

5. Select the facial expression that matches your current feeling.

very happy   good!   angry   I want to avoid   sad

6. What is the color of your feeling?

(1) What is the color when you are sad?
   (2) What is the color when you are angry?
   (3) What is the color when you are happy?

FIG. 5

CATS_KID questionnaire 1

Check or fill in the blank that applies to you.

1. Are you a boy or a girl?
   ☐ ☑

2. How old are you? ( 7 )

3. How many brothers and sisters do you have?

| ☑ Older brother | 1 | ☐ Younger brother | |
   |---|---|---|---|
   | ☐ Older sister | | ☐ Younger sister | |

4. Your father is?
   ☑ Real father  ☐ Step father  ☐ I don't have a father

5. Your mother is?
   ☑ Real mother  ☐ Step mother  ☐ I don't have a mother

6. Check the box for your family members who live with you or fill in the blank.

| ☑ Father | ☐ Mother |
   |---|---|
   | ☐ Older brother ( 1 ) | ☐ Older sister ( ) |
   | ☐ Younger brother ( ) | ☐ Younger sister ( ) |
   | ☐ Grandfather | ☐ Grandmother |
   | ☐ Other ( ) | |

If you did not check the box for your father or your mother, why didn't you check the box?
   ☐ Your father or mother is not living with you because of the work
   ☐ Your parents are separated    ☐ Your parents are divorced
   ☐ Your father left your home    ☐ Your mother left your home
   ☐ Your parents passed away     ☐ other ( )

COMPUTER SYSTEM AND COMPUTER-READABLE STORAGE MEDIUM FOR ART THERAPY

CROSS-REFERENCE TO RELATED APPLICATIONS

This application is the national phase under 35 U.S.C. §371 of PCT International Application No. PCT/KR2009/006325, filed on Oct. 30, 2009, which claims the benefit of Korean Patent Application No. 10-2008-0107289, filed Oct. 30, 2008. The entire contents of the aforementioned applications are hereby incorporated herein by reference.

CROSS-REFERENCE TO RELATED APPLICATIONS

This application claims the benefit of Korean Patent Application No. 10-2008-0107289, filed with the Korean Intellectual Property Office on Oct. 30, 2008, the disclosure of which is incorporated herein by reference in its entirety.

BACKGROUND

1. Technical Field

The present invention is related to a computer system for art therapy and a computer-readable storage medium in which a program of instructions for art therapy is stored, more specifically to a computer system and a computer-readable storage medium that can contribute to the art therapy through an analysis and evaluation of data with objectivity, consistency, reliability and validity.

2. Description of the Related Art

Art therapy has been widely recognized as a useful tool that can diagnose the psychological, personality and intellectual status of a person who paints or draws, detect changes in the person's status and also improve the person's status. Tests such as House-Tree-Person (HTP), Draw A Person (DAP) and Kinetic Family Drawings (KFD) are techniques called the "projection method," which is developed in the field of psychology for its own purposes.

Meanwhile, in the field of art therapy, various techniques called art therapy assessment have also been developed for its own purposes. Such techniques include Descriptive Assessment of Psychiatric Artwork (DAPA), Diagnostic Drawing Series (DDS), A Person Picking an Apple from a Tree (PPAT), Face Stimulus Assessment (FSA), Ulman Personality Assessment Procedure (UPAP), Silver Test and Favorite Kind of Day (FKD). However, these art therapy techniques or art therapy assessments still have many problems in objectivity, consistency, reliability and validity because they are easily dependent on art therapist's subjective experience, knowledge and judgment.

SUMMARY

The present invention provides a computer system that improves the objectivity, consistency, reliability and validity of an analysis and evaluation of data by automatically performing the analysis and evaluation for art therapy.

The present invention also provides a computer-readable storage medium, in which a program of instructions is stored, that improves the objectivity, consistency, reliability and validity of an analysis and evaluation of data.

Other problems that the present invention solves will become more apparent through the following embodiments described below.

To achieve the foregoing objectives and resolve the problems of the related art, an aspect of the present invention provides a computer system that includes a drawing module, which presents a plurality of patterns and selects a certain pattern and composes and colors a drawing according to working of a person tested for art therapy, an analysis module, which analyzes one or more factors from the colored drawing, a parsing module, which evaluates a psychological state, symptom or disorder of the person tested for art therapy from the analyzed factors, and a database including a pattern library, in which the plurality of patterns are stored, drawing process information, which is about drawing processes of selecting the pattern and composing and coloring the drawing, and art therapy knowledge.

Another aspect of the present invention provides an art therapy method that includes providing a plurality of patterns to a person tested for art therapy, drawing a picture by selecting, composing and coloring a certain pattern according to working of the person tested for art therapy, analyzing a plurality of factors from the picture, and evaluating psychological state, symptoms or disorders of the person tested for art therapy by using art therapy knowledge in which the plurality of factors are matched against the psychological state, symptoms or disorders.

Still another aspect of the present invention provides a computer-readable storage medium that includes providing a plurality of patterns to a person tested for art therapy, drawing a picture by selecting, composing and coloring a certain pattern according to working of the person tested for art therapy, analyzing a plurality of factors from the picture, and evaluating psychological state, symptoms or disorders of the person tested for art therapy by using art therapy knowledge in which the plurality of factors are matched against the psychological state, symptoms or disorders.

Additional aspects and advantages of the present invention will be set forth in part in the description which follows, and in part will be obvious from the description, or may be learned by practice of the invention.

DETAILED DESCRIPTION

Since there can be a variety of permutations and embodiments of the present invention, certain embodiments will be illustrated and described with reference to the accompanying drawings. This, however, is by no means to restrict the present invention to certain embodiments, and shall be construed as including all permutations, equivalents and substitutes covered by the spirit and scope of the present invention. Throughout the drawings, similar elements are given similar reference numerals. Unless clearly used otherwise, expressions in the singular number include a plural meaning. In the present description, an expression such as "comprises/includes" or "consisting/including" is intended to designate a characteristic, a number, a step, an operation, an element, a part or combinations thereof, and shall not be construed to preclude any presence or possibility of one or more other characteristics, numbers, steps, operations, elements, parts or combinations thereof.

A computer system for art therapy according to an embodiment of the present invention presents a plurality of patterns to a person tested for art therapy through a display module, for example, a monitor, and can evaluate the psychological status, symptoms or disorders of the tested person by selecting a certain pattern and composing and coloring a drawing and then automatically analyzing the colored drawing according to the working of the person tested for art therapy. Here, the plurality of patterns can be, for example, Kinetic Family Drawings (KFD), Kinetic School Drawings (KSD), Drawing A Person (DAP), Drawing A Group (DAG), House-Tree-Person (HTP) or Mandala. However, the patterns are not limited to the above-described examples, and it is possible that various patterns can be applied as long as the patterns are for psychotherapy. The person tested for art therapy draws a drawing such as Kinetic Family Drawings, Kinetic School Drawings, Drawing A Person, Drawing A Group, House-Tree-Person or Mandala by using the presented patterns. The computer system analyzes a plurality of factors (for example, color-related factors, space-related factors, shape-related factors, behavior-related factors, performance-related factors and the like) for evaluating the psychological status, symptoms or disorders from the drawing. Then, the psychological status, symptoms or disorders of the person tested for art therapy can be evaluated from the analyzed factors. The evaluation can be performed by using the art therapy knowledge matched between the analyzed factors and the psychological status, symptoms or disorders and personality information obtained from the person tested for art therapy. As such, the evaluation can be performed automatically and precisely by performing the evaluation of the drawing through the computer system. Moreover, changes in psychological symptoms or disorders of the tested person for art therapy can also be evaluated by repeating the computer system several times and detecting changes in the drawing.

Below, using the Kinetic Family Drawings for art therapy is an example of a computer system and a recorded medium readable by a computer in accordance with an embodiment of the present invention. However, it shall not limit the scope of the claims of the present invention and be apparent that using patterns for psychotherapy, for example, the Kinetic School Drawings (KSD), Drawing A Person (DAP), Drawing A Group (DAG), House-Tree-Person (HTP) and the like, can be included in the scope of the claims of the present invention. The present invention will be described in more detail hereinafter through certain embodiments of the present invention, which will be described later.

Figure 1:
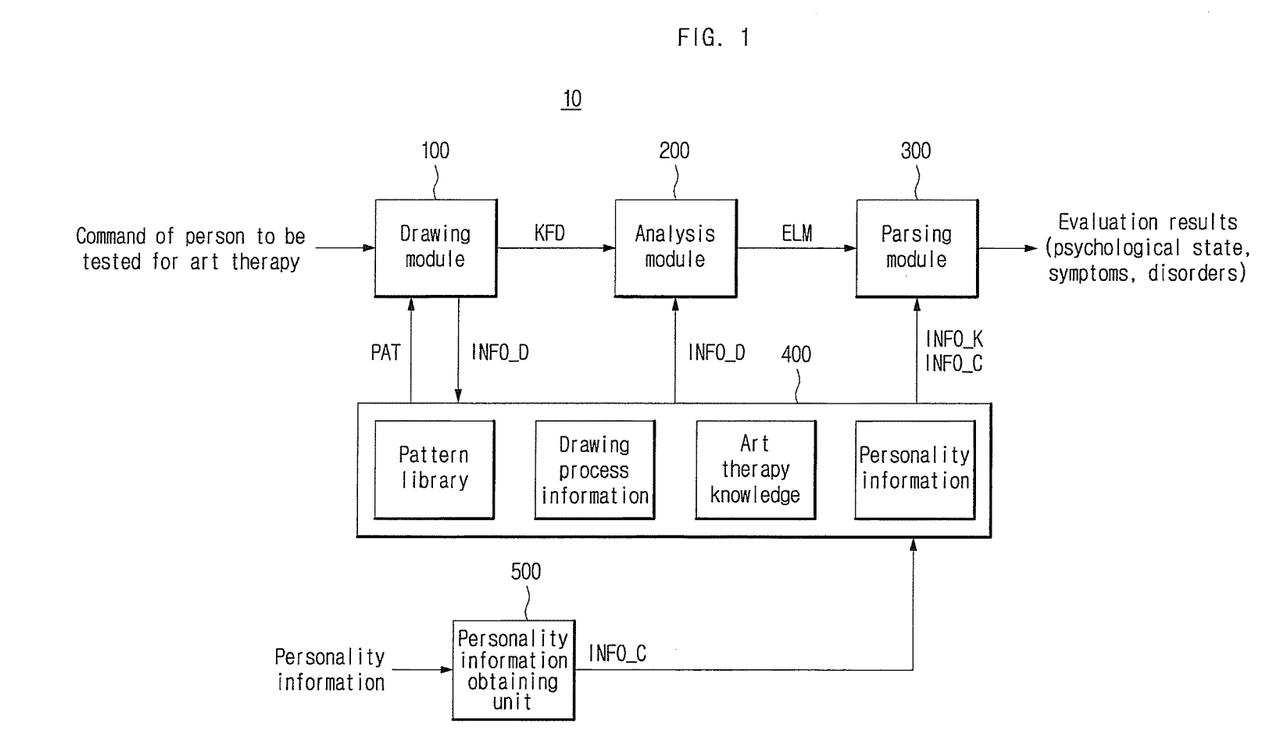
FIG. 1 is a block diagram of a computer system in accordance with an embodiment of the present invention.
Figure 3:
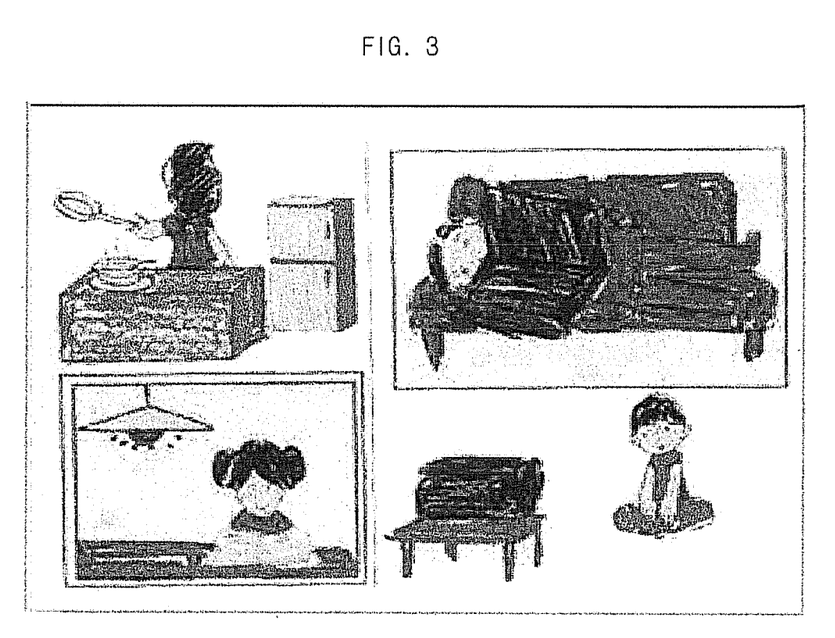
FIG. 3 is an example of Kinetic Family Drawings.
Figure 4:
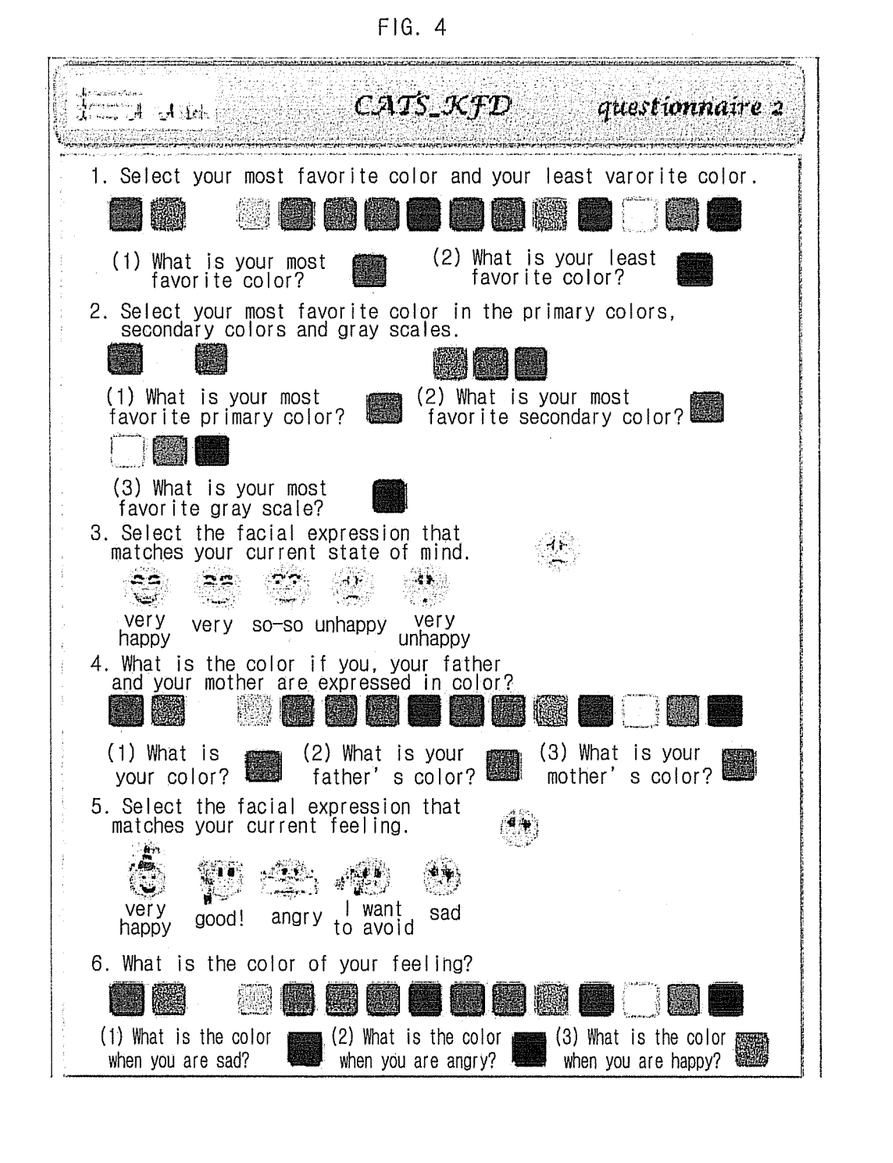
FIGS. 4 and 5 show examples for describing the steps of obtaining the personality information of a person tested for art therapy.
Figure 5:
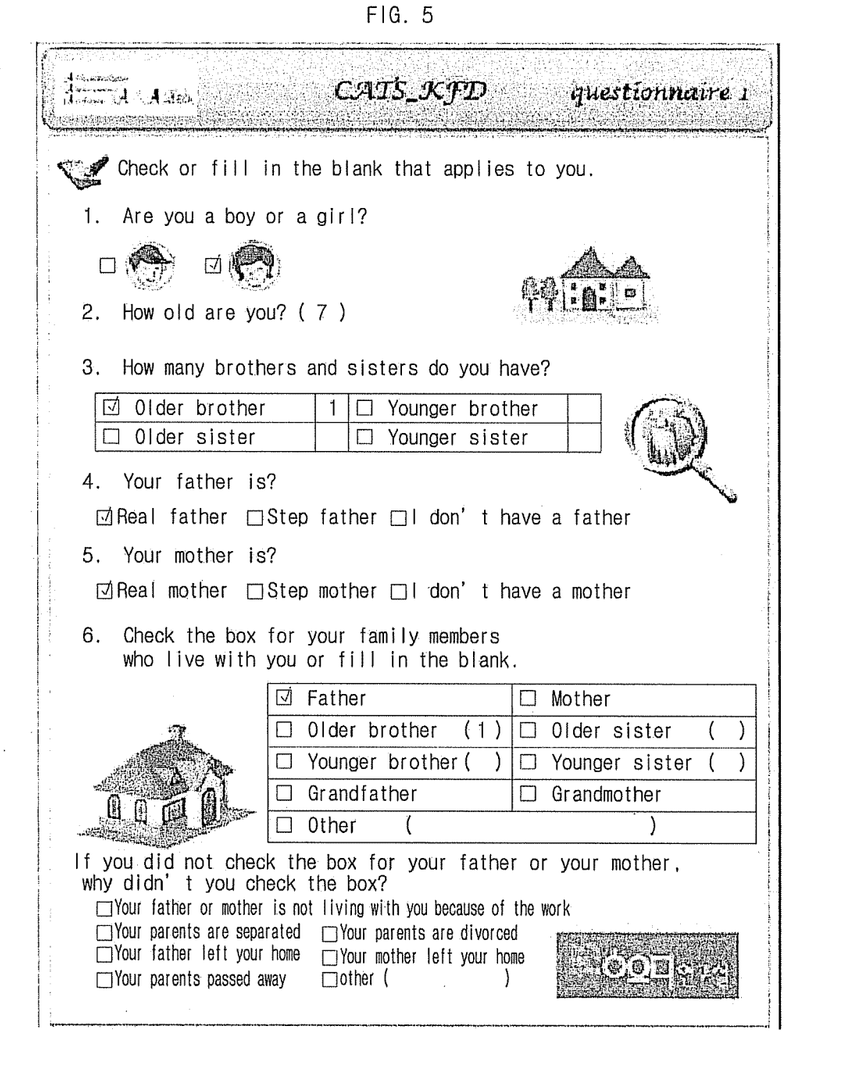

First of all, in the present embodiment, a computer system for art therapy and a recorded medium, in which a program for art therapy is stored, readable by a computer will be described with reference to FIGS. 1 to 5. FIG. 1 is a block diagram of a computer system according to an embodiment of the present invention, FIG. 2 shows an example for describing the drawing module of FIG. 1, FIG. 3 is an example of Kinetic Family Drawings, and FIGS. 4 and 5 show examples for describing the steps of obtaining the personality information of a person to be treated for art therapy.

First, with reference to FIG. 1, a computer system 10 according to an embodiment of the present invention includes a drawing module 100, an analysis module 200, a parsing module 300 and a database 400.

The drawing module 100 presents a plurality of patterns to a person to be tested for art therapy, and then draws Kinetic Family Drawings by selecting certain patterns and composing and coloring a drawing according to the working of the tested person for art therapy.

Figure 2:
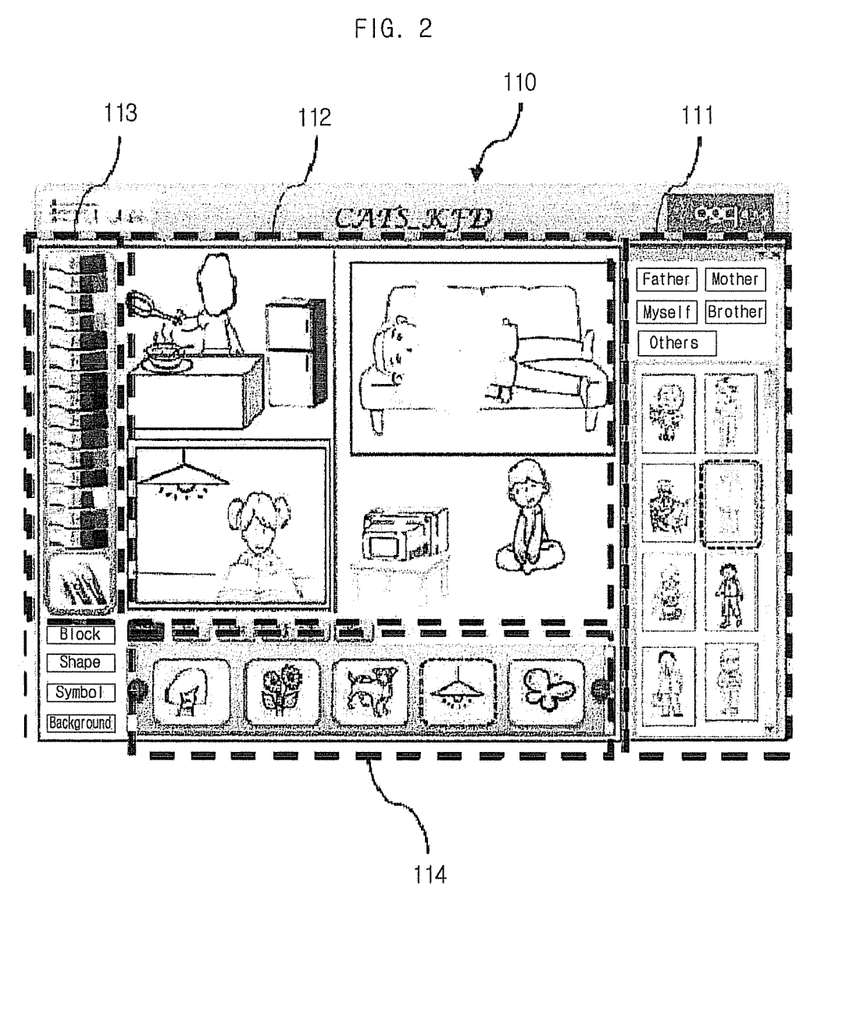
FIG. 2 shows an example for describing the drawing module of FIG. 1.

In explanation of the drawing module 100 in more detail with reference to FIG. 2, the drawing module 100 is displayed by a display module 110, for example, a monitor such as an LCD or PDP, to the person to be tested for art therapy, and the working of the tested person are inputted into the drawing module 100 by the display module 110. Here, the display module 110 can have a display resolution of 1024×768 or 1280×800, and the tasks of the tested person includes selecting a pattern, arranging the selected pattern, composing drawings, coloring and the like. A series of actions (for example, the selection of patterns, the configuration of drawings and colorings) by the tested person for art therapy can be displayed through the display module 110.

The drawing module 100 will be described in more detail hereinafter.

The drawing module 100 presents to the tested person for art therapy through a family window 111 a plurality of patterns which represent family members and the behavior of each of the family members and gets input from the tested person through the family window 111, in which the input is the working of the tested person. In the case of a father, for example, the family window 111 presents a plurality of patterns such as reading a book, watching television, talking, playing with the children, going to work, scolding, and drinking. In the case of a mother, for example, the family window 111 presents a plurality of patterns such as cooking, washing dishes, making the bed, playing with family members, cleaning, ironing, planting, and sewing. In the case of a boy, for example, the family window 111 presents a plurality of patterns such as playing, eating, throwing a ball, riding a bicycle, and watching television. In the case of a girl, for example, the family window 111 presents a plurality of patterns such as playing, eating, walking, riding a bicycle, and washing dishes. Therefore, if the person tested for art therapy selects a certain pattern by clicking on it at the family window 111 and drags it to an operation window 112, the drawing module 100 can arrange the selected pattern on the operation window 112 accordingly.

Here, the plurality of patterns (PAT) are predrawn patterns, which are prestored in a pattern library, and the drawing module 100 can present the plurality of patterns (PAT) to the person to be tested for art therapy by reading them from the pattern library. Although FIG. 1 shows that the pattern library is included in a database, which will be described later, it shall be apparent that the present invention is not limited to this example and the pattern library can be included in the drawing module 100.

Furthermore, the drawing module 100 presents to the person tested for art therapy through a color window 113 a plurality of colors for coloring the selected pattern and brushes for coloring the pattern and gets input from the tested person through the color window 113, in which the input is selection of a color and a brush used for coloring. Accordingly, the tested person selects a color and a brush from the color window 113, and can color the selected pattern by moving a mouse on the operation window 112, as illustrated in FIG. 3. Here, a plurality of brushes having different thicknesses can be provided. As such, allowing the person tested for art therapy to select coloring tools of various thicknesses is for analyzing factors related to the performance of the tested person (for example, completeness, accuracy and concentration) and the skill level of using one's hand. Analyzing the completeness, accuracy and concentration will be described later.

Also, the drawing module 100 can include a symbol widow 114 and a background window such that the tested person can select a pattern other than those of the family members on the operation window 112.

For example, the symbol window 114 can present a cleaner, a dining table, a chair, a piano, a washing machine, a newspaper, a book, scissors, a knife, a dressing table, a doll, a bed, an iron, a sofa and a refrigerator, which are placed in the house, a lawn-mower, a trash can, a ball, a jump rope, a kite, a ladder, a car, a train, water, a house and a building, which are placed outside the house, a butterfly, a cat, a snake, a dog, a flower, a tree, leaves and a log, which represent animals and plants, and rain, snow, the sun, the moon, stars, clouds and sleets, which represent weather conditions.

The background window presents a room, a bedroom, a kitchen, a living room, a study, a bathroom, an inside of the house, a front of the house, a school, a front of a building, a shopping mall, a restaurant, a hospital, a swimming pool, a church, a field, a playground, an inside of a car, a garden, a fishing place, a mountain, a sea and a road.

The drawing module 100 can also present through a block window a block form so as to block an area in the operation window 112 and present through a figure window a figure such as a triangle, a rectangle, a circle, an arrow, a line and a dotted line. It can also be presented through the background window that a background can be set into the operation window 112. Such patterns presented through the symbol window 114, the background window, the block window and the figure window are stored in the pattern library.

As such, the drawing module 100 presents the plurality of patterns to the person tested for art therapy through the display module 110, and colors each pattern through the display module 110 by arranging the selected patterns on the operation window 112 and composing the Kinetic Family Drawings according to the working of the tested person.

When composing the Kinetic Family Drawings, the drawing module 100 can compose the Kinetic Family Drawings by expanding, reducing, rotating or deleting a certain portion of the patterns according to the working of the tested person. Here, the drawing module 100 can independently perform vertical expansion, vertical reduction, horizontal expansion and horizontal reduction of each portion of the patterns, according to the working of the tested person. This is for determining the sense of balance in the tested person. However, the scope of the present invention does not exclude that the vertical expansion and the horizontal expansion are performed at the same time and the vertical reduction and the horizontal reduction are performed at the same time.

Furthermore, the drawing module 100 can compose the Kinetic Family Drawings by blocking the patterns using the block window. In a more detailed example, the drawing module 100 can select and arrange a mother who is cooking, select and arrange a sister who is reading a book in a room, select, rotate and arrange a father who is reading a newspaper and arrange himself/herself who is watching TV, through the working of the person tested for art therapy, like the Kinetic Family Drawings that is drawn in the operation window 112 of FIG. 2. The drawing module 100 can also distinguish the father and the sister by the block window, expand his/her hands, delete the mother's facial features and compose the Kinetic Family Drawings through the working of the person tested for art therapy.

Meanwhile, the drawing module 100 can store information (INFO_D) about these drawing processes into the database 400. Here, the drawing process information (INFO_D) is a series of processes that are performed according to the working of the person tested for art therapy, and can include, for example, information about the selection of patterns, such as the length of time used to select the patterns, information about the composition of the Kinetic Family Drawings, information about the coloring of the patterns and the like. Here, the information about the selection of patterns represents the forms and types of the selected patterns and a sequence in which the patterns are selected. The information about the composition of the Kinetic Family Drawings is information about the placement of the patterns, the partial expansion, reduction, rotation and deletion of the patterns, grouping of the patterns, a process in which a pattern is deleted after being placed, and the areas of the patterns, and can represent information about things performed by the drawing module 100 according to the working of the person tested for art therapy while the patterns are selected and colored by the person tested for art therapy. The information about the coloring of the patterns can represent the types of colors, the areas of the colors and the thicknesses of coloring tools.

Meanwhile, the analysis module 200 of FIG. 1 analyzes at least one factor from the Kinetic Family Drawings completed through the drawing processes. For example, the analysis module 200 can analyze a factor related to color, a factor related to performance, a factor related to space, a factor related to form and a factor related to behavior. The factor related to performance includes an accuracy factor, a completeness factor and a concentration factor. Here, the drawing process information (INFO_D) stored in the database 400 can be used. An analysis process for each factor will be described in more detail hereinafter.

First, the analysis module 200 analyzes the factor related to color by measuring at least one of the following: the number colors used in the patterns, the types of colors used in the patterns, the sequence of coloring, the intensity of coloring, the mixing of colors, color clusters (a collection of same colors that are connected), complementary colors, colors used in the entire drawings, colors used in people, the area for each color, the theme color (the most frequently used color), the sub-theme color (the second most frequently used color), the ratio between primary colors (red, blue and yellow) and secondary colors (green, violet and orange) and the ratio between warm colors (red, orange and yellow) and cool colors (blue and indigo blue).

Taking an example of the analysis module 200 recognizing and measuring the color used in each pixel of the display module 110, the area for each color can be measured by the number of pixels occupying an area colored in one color. The theme color and the sub-theme color can be determined according to the number of pixels occurred by each color. The ratio between the primary colors and the secondary colors and the ratio between the warm colors and the cool colors can be also measured by the ratio of the number of pixels.

Alternatively, the analysis module 200 can recognize the colors by color-scanning the completed drawing on the screen of the display module 110, and can analyze the factors related to color. The analysis module 200 can recognize and analyze what the digital data of the colors used in coloring are because the drawing module 100 allows the person tested for art therapy to select the prepared colors to color. In this case, each color and its corresponding data can be prepared in the form of a lookup table. To analyze the factor related to time, like the coloring sequence, the analysis module 200 can use the drawing process information (INFO_D) stored in the database 400.

The analysis module 200 can also analyze the factors related to performance constituted by the accuracy factor, completeness factor and concentration factor of a work representing the performance.

The analyzing of the factor related to performance will be described in more detail hereinafter.

First, the analyzing of the factor related to performance begins from analyzing the completeness factor and the accuracy factor.

To analyze the completeness factor, the analysis module 200 can measure the number of pixels in a colored pattern against the number of pixels in the entire selected pattern.

Also, the accuracy factor is measured by the degree of matching between the clusters of patterns and the clusters of colors. The pattern clusters represent an area distinguished by the outline of the patterns, and the color clusters represent an area distinguished by colors. The matching of the pattern clusters and the color clusters can be, for example, measured by the number of pixels occupying the pattern clusters and the number of pixels occupying the color clusters.

The concentration factor can be analyzed by using a step regression analysis and standard regression analysis method of a multiple linear regression analysis, in which the above-described color related factor, completeness related factor and accuracy related factor are explanatory variables.

The regression analysis methods will be described hereinafter.

Analysis target drawing samples in the quantity of n are collected, and their concentrations are evaluated and ranked by m evaluators. The drawing with the highest concentration is ranked first, and the drawing with the lowest concentration is ranked nth.

The rank average of the m evaluators against an analysis target drawing sample i is expressed as Yi. The multiple linear regression analysis method is applied by expressing the number of colors of each sample as Xi1, the number of clusters as Xi2, the completeness as Xi3, and the accuracy as Xi4. Then, Mathematical Equation 1 below shows a regression analysis model.

$$Yi = \beta 0 + \beta 1 \ Xi1 + \beta 2 \ Xi2 + \beta 3 \ Xi3 + \beta 4 \ Xi4 + \epsilon i, \ i = 1, 2, \ldots, n$$ [Mathematical Equation 1]

Here, it shall be assumed that each εi is independent from one anther and has a normal distribution with the average and dispersion of 0 and σ2, respectively.

β0 is a coefficient of a constant number, β1 is a coefficient of the number of colors, β2 is a coefficient of completeness, and β4 is a coefficient of accuracy. The signs of β1, β2, β3 and β4 are negative. As the number of colors and the number of clusters become greater, and as the completeness and the accuracy become greater, the ranking value, which is a dependant variable, becomes smaller. That is, the concentration becomes greater.

A result of standard regression analysis, which uses a standardized value (the following values) to determine relative influence with respect to the concentration of each independent variable, is also provided.

$$Yi' = \{(Yi - S(Y)\}/S(Y),$$

$$Xij' = \{(Xij - S(Xj)\}/S(Xj), i=1,2,\ldots,n, j=1,2,3,4$$

Here, S(Y) and S(Xj) represent the sample standard deviation of Y and Xj, respectively.

The analysis module 200 can analyze the space-related factors by measuring at least one of the length, size, rotation and separation of the pattern selected from the drawing and a distance, direction and the number of obstacles between the patterns. For example, the analysis module 200 can analyze where the family members are placed from the center of the operation window 112, whether the family members are intentionally separated from one another by using the plurality of obstacles between the family members, the direction of each of the family members, the distance between the family members, the block window or lines, whether all family members are placed at the edge of the operation window 112, the degree of space utilization of the operation window 112 and the like.

More specifically, the analysis module 200 can measure the length of a pattern by measuring the distance between two pixels presented at a certain location among the pixels occupying the selected pattern, and can measure the size of the pattern by measuring the number of pixels occupying each pattern. Also, the distance between each pattern can be measured by determining a representative pixel for each pattern and then measuring the distance between the determined representative pixels. Here, the representative pixel can be a pixel that is positioned at the center among the pixels occupied by each pattern or a pixel of averge coordinates, which are the average coordinates of the pixels occupied by each pattern. As such, the analysis module 200 analyzes the space-related factors by using pixels, allowing an accurate, precise and objective analysis.

Furthermore, the analysis module 200 can analyze the form-related factors and the behavior-related factors by recognizing the forms and types of patterns constituting the drawing and the behavior of the patterns.

More specifically, the analysis module 200 analyzes the form-related factors such as the length of arms or legs of the family members, whether all parts of the body are drawn, whether all figures are drawn, whether all brothers and sisters are drawn, whether the parents are drawn, the size of each family member, whether the teeth of each family member are drawn, the facial expression of the family members, whether a family member is deleted after he or she is drawn, whether there is a description of each pattern, the distance between the family members, whether each pattern is rotated, and whether shades are drawn.

Furthermore, the analysis module 200 can analyze the behavior-related factors depicted in the drawing module 100 according to the working of the person tested for art therapy, based on whether a pattern is selected and arranged to show each family member having a certain behavior, whether a pattern is selected and arranged to show each family member communicating with other family members, whether a pattern is selected and arranged to show each family member working together with other family members, and whether a pattern is selected and arranged to show himself/herself being abused.

The analysis of the form-related factors and the behavior-related factors is related to how the person tested for art therapy selects and arranges the patterns representing certain behaviors or patterns representing certain forms. As these patterns are prestored in the pattern library, the analysis module 200 can analyze these form-related factors and behavior-related factors quickly, objectively and accurately.

Meanwhile, the parsing module 300 evaluates the psychological state, symptoms and disorders of the person tested for art therapy from the factors analyzed by the analysis module 200. Here, the parsing module 300 can use art therapy knowledge (INFO_K), which is prestored in the database 400.

The database 400 includes the pattern library, the drawing process information (INFO_D), the art therapy knowledge (INFO_K) and personality information (INFO_C).

As described above, the pattern library stores a plurality of patterns presented through the family window 111, the block window, the figure window, the symbol window 114 and the background window.

Table 1 below is an example of the art therapy knowledge (INFO_K) prestored in the database 400.

TABLE 1

| | [Index] Art therapy knowledge (Reliability Rate) |
|---|---|
| Form related | [Knowledge S1] If the tested person is not included, the tested person is usually a sexually abused child (4). |
| | [Knowledge S2] If a person is drawn to show his or her back, it means that the child has a negative attitude and repressive anger at that person (3). |
| | [Knowledge S3] If things such as electric light, lamps, TV and the sun are drawn, this reflects the desire for love and affection (1). |
| | [Knowledge S4] If any form seems to have lost a sense of direction, the child is from a family that has neglected in protecting the child (2). |
| Behavior related | [Knowledge A1] If a boy draws himself riding a bicycle or a horse, he has a learning disorder, anxiety disorder, panic disorder, attention-deficit, hyperactivity disorder and behavioral (conduct) disorder (2). |
| | [Knowledge A2] If a boy draws himself playing, he is normal (5). |
| | [Knowledge A3] If members of a family show a same behavior, this means that the family members communicate and cooperate with one another well (4). |
| Color related | [Knowledge C1] If the number of colors used is two or less, he or she has experienced a serious sexual abuse (2) or is depressed (3). |
| | [Knowledge C2] The percentage of red exceeds 50%, the tested person is psychologically and emotionally unstable (1). |
| | [Knowledge C3] If most frequently used color is the same as the color used to draw his or her mother, he or she is closer to the mother than the father (1). |
| | [Knowledge C4] If most frequently used color is black, the tested person has psychological trauma, depression and despair (4). |
| | [Knowledge C5] If the sun is colored in black, the tested person has experienced psychological trauma (4). |
| | [Knowledge C6] If a house is colored in red, the tested person has been sexually abused. |
| Space related | [Knowledge E1] If a child is isolated or a member of the family is isolated from the others, the child has a parent with alcohol and/or substance abuse problem (2). |
| | [Knowledge E2] If a boy draws himself very close to his mother, he has a learning disorder, anxiety disorder, panic disorder, attention-deficit, hyperactivity disorder and behavioral (conduct) disorder (1). |
| | [Knowledge E3] If a member of the family is separated from the others, communication and relationship between the member and the others are cut off (3). |
| | [Knowledge E4] If someone is drawn bigger, that person is respected or authoritative (4). |
| | [Knowledge E5] If a distance between two people is drawn close to each other, the two members are intimate with each other (3). |
| | [Knowledge E6] If a distance between two people is drawn far away from each other, there is an emotional separation between the two members (3). |
| | [Knowledge E7] If a person is drawn on a lower portion, that person is depressed or experiences a lack of energy (2). |
| | [Knowledge E8] If a person is drawn on an upper portion, he or she is actually the center figure of the family (4). |
| | [Knowledge E9] If family members are not separated from one another, the family members communicate and cooperate with one another very well (2). |
| Performance related | [Knowledge P1] If the completeness is less than or equal to 30%, the tested person is weary of everything (3). |
| | [Knowledge P2] If the accuracy is less than or equal to 30%, the tested person has an attention deficit disorder (2). |
| | [Knowledge P3] If the concentration is within 20 percentile, the tested person has a peace of mind (4). |

As shown in Table 1, the art therapy knowledge (INFO_K) can be expressed in the form of "if" and "then" according to the selection and arrangement of each pattern and the composition and coloring of the drawing, and the reliability rate can be scored for each knowledge. Such knowledge and scores can be changed through an update process, and can be used variously in analyzing psychological symptoms and disorders through the changes of the knowledge and scores. Although the knowledge and scores are changed, the knowledge and scores can be analyzed easily, fast and accurately since they are analyzed by a computer.

The personality information (INFO_C) can be obtained from a personality information obtaining unit 500 and stored in the database 400. Such personality information (INFO_C) can include, for example, information about the family relationship and color preference of the person tested for art therapy.

Meanwhile, the parsing module 300 can evaluate the psychological state, symptoms and disorders of the person tested for art therapy from the factors (ELM) analyzed by the analysis module 200 by using the personality information (IN- FO_C) obtained from the tested person stored in the database 400. An example of the personality information (INFO_C) stored in the database 400 is shown in Table 2.

TABLE 2

| | (Index) Personality information |
|---|---|
| Family relationship | (Situation 1) Have parents |
| | (Situation 2) Have a brother. |
| | (Situation 3) 7-year old girl. |
| Color preference | (Situation 4) Father's color is blue. |
| | (Situation 5) Mother's color is green. |
| | (Situation 6) Favorite color is red. |
| | (Situation 7) Least favorite color is black. |

Such personality information (INFO_C) can be obtained in advance through a survey, as illustrated in FIGS. 4 and 5. A method of obtaining the personality information (INFO_C) is not limited to this example, and information learned through the observation of an expert can be stored in the database 400 by the expert.

Figure 6:
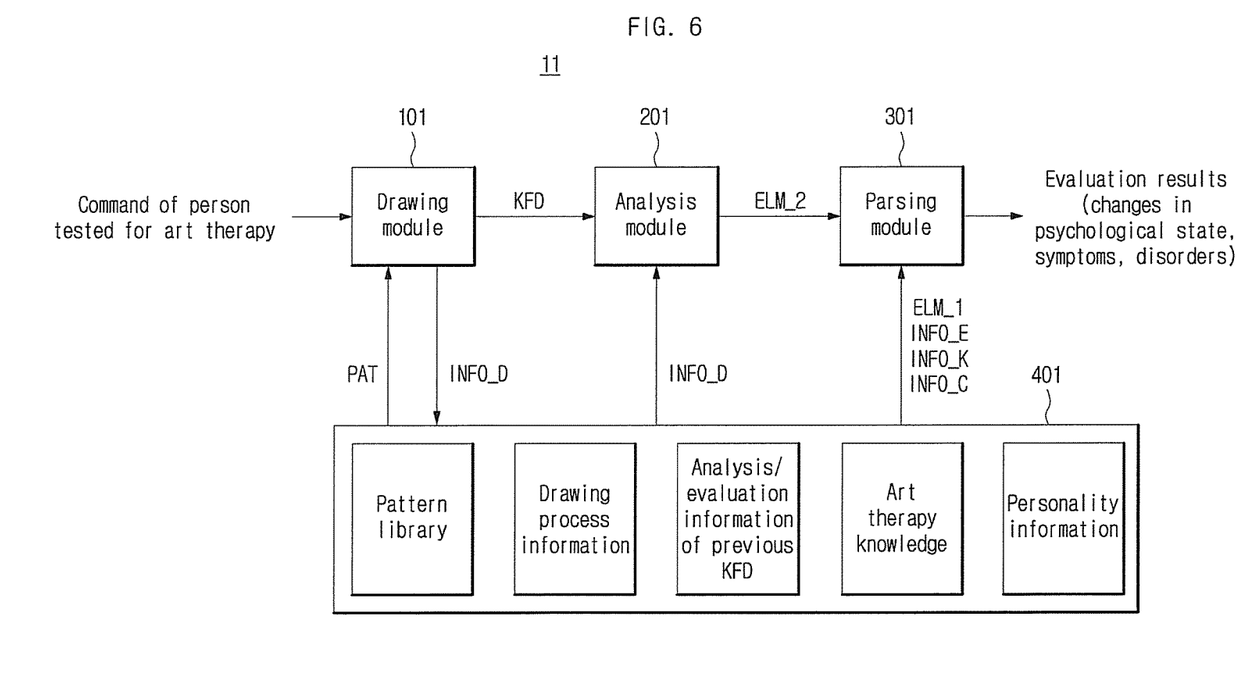
FIG. 6 is a block diagram for describing a computer system in accordance with another embodiment of the present invention.
Figure 7:
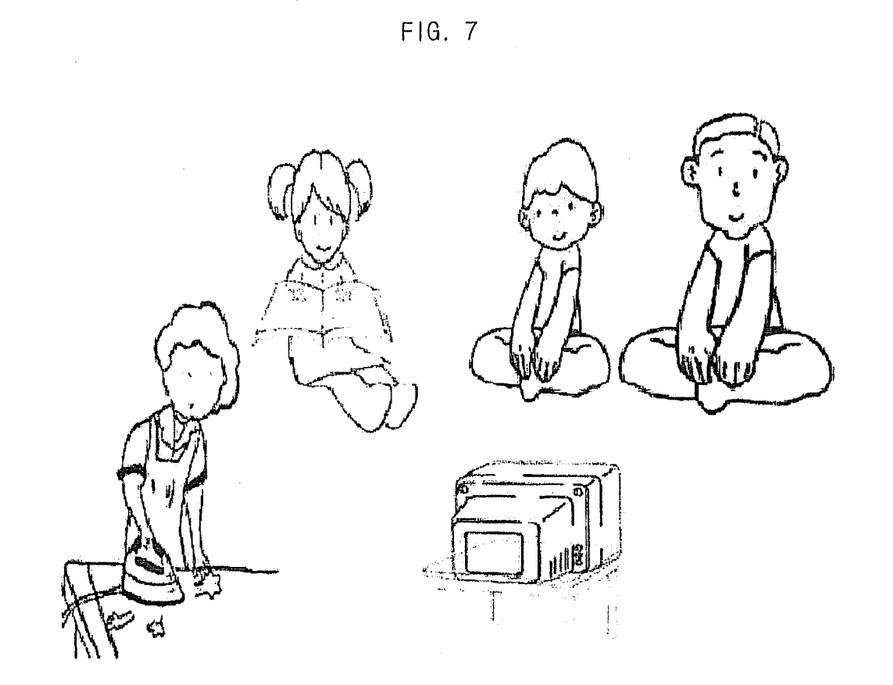
FIGS. 7 and 8 are other examples of Kinetic Family Drawings.
Figure 8:
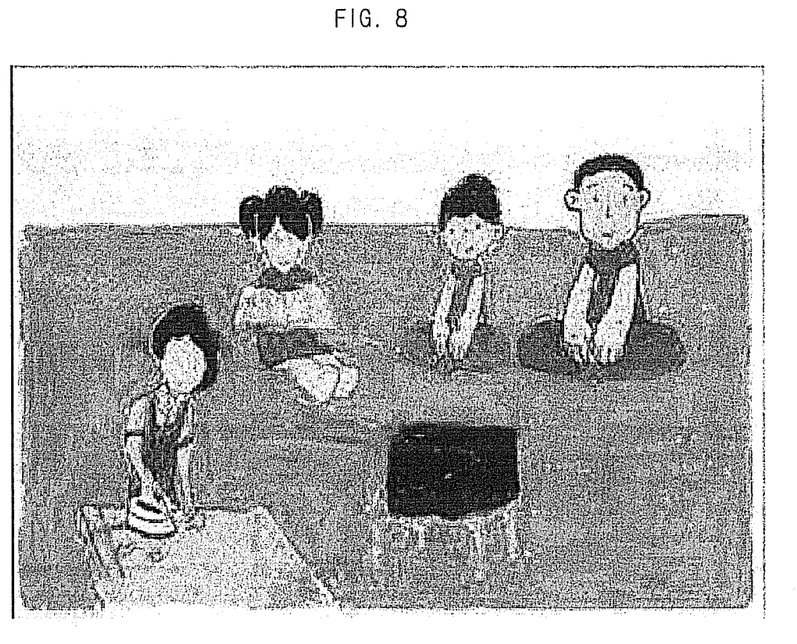

Next, a computer system and a recorded medium readable by a computer in accordance with another embodiment of the present invention will be described below with reference to FIGS. 6 to 8. FIG. 6 is a block diagram for describing a computer system in accordance with another embodiment of the present invention, and FIGS. 7 and 8 are other examples of the Kinetic Family Drawings. Those components that are the same or are in correspondence with those of FIG. 1 are rendered the same reference numeral regardless of the figure number, and redundant descriptions are omitted.

In FIG. 6, a computer system 11 of the present embodiment evaluates changes in psychological state, changes in symptoms or changes in disorders of the person tested for art therapy, by considering analysis information (ELM_1) and evaluation information (INFO_E) of the drawing that is previously drawn by the working of the person tested for art therapy.

More specifically, analysis information of previous Kinetic Family Drawings (i.e., a factor (ELM_1) that is analyzed previously by an analysis module 201 from the previous Kinetic Family Drawings) is stored in a database 401.

Once a drawing module 101 draws Kinetic Family Drawings according to the working of a person tested for art therapy, the analysis module 201 outputs a factor (ELM_2) that is analyzed from the currently drawn Kinetic Family Drawings to a parsing module 301.

The parsing module 301 can evaluate changes in psychological state, changes in symptoms or changes in disorders of the person tested for art therapy by reading the factor (ELM_1), analyzed from the previous Kinetic Family Drawings, from the database 401, by comparing the factor (ELM_2), analyzed from the currently drawn Kinetic Family Drawings, with the factor (ELM_1), analyzed from the previously drawn Kinetic Family Drawings, and by using the personality information (INFO_C) and the art therapy knowledge (INFO_K). Here, the art therapy knowledge (INFO_K) can be knowledge in which changes in each factor match changes in psychological state, changes in symptoms or changes in disorders.

Furthermore, by repeatedly running the computer system, the analysis information (ELM_1) and evaluation information (INFO_E) of previous drawings can be accumulated. Such accumulated information is stored in the database 401 and then used in the parsing module 301.

For example, if the Kinetic Family Drawings in FIGS. 2 and 3 are previously drawn Kinetic Family Drawings and the Kinetic Family Drawings in FIGS. 7 and 8 are currently drawn Kinetic Family Drawings, the parsing module 301 receives factors (ELM_1 and ELM_2) like those in Table 3. In Table 3, any analysis information indicated with "(First session)" is a factor (ELM_1) that is analyzed from previously drawn Kinetic Family Drawings and read from the database 401, and any analysis information indicated with "(Second session)" is a factor (ELM_2) that is analyzed from currently drawn Kinetic Family Drawings and provided from the analysis module 201.

The parsing module 301 can evaluate changes in psychological state, symptoms or disorders of the person tested for art therapy by using the personality information (INFO_C) and the art therapy knowledge (INFO_K) from the changes of the factors (ELM_1 and ELM_2). For example, if the mother is not separated in a block according to the currently analyzed factor (ELM_2) even though the mother was separated in a block according to the previously analyzed factor (ELM_1), the parsing module 301 can evaluate, by using the art therapy knowledge (INFO_K), from the change in the separation status of the mother that communication and cooperation between the family members are changed and the relationship between them has improved.

TABLE 3

| Assessment information for each session |
|---|
| (Situation 8) Father lies on the floor and reads a newspaper (First session). He is watching TV (Second session). |
| (Situation 9) Father is separated from others (First session). N/A (Second session). |
| (Situation 10) Father is placed in an upper area (First session). N/A (Second session). |
| (Situation 11) Father's length is 327 pixels (11.45 cm) (First session). Father's length is 269 pixels (9.41 cm) (Second session). |
| (Situation 12) Father occupies an area of 25,594 pixels (31.35 cm$^2$) (First session). Father occupies an area of 28,936 pixels (35.45 cm$^2$) (Second session). |
| (Situation 13) Mother is in the kitchen while showing her back (First session). She is ironing (Second session). |
| (Situation 14) Mother is separated from others (First session). N/A (Second session). |
| (Situation 15) Mother's length is 5.60 cm (First session). Mother's length is 8.89 cm (Second session). |
| (Situation 16) Mother occupies an area of 10.54 cm$^2$ (First session). Mother occupies an area of 13.67 cm$^2$ (Second session). |
| (Situation 17) Brother is watching TV. No change (Second session). |
| (Situation 18) Brother's length is 6.30 cm (First session). Brother's length is 8.26 cm (Second session). |
| (Situation 19) Brother occupies an area of 12.13 cm$^2$ (First session). Brother occupies an area of 18.06 cm$^2$ (Second session). |

TABLE 3-continued

Assessment information for each session (Situation 20) The tested person is studying (First session). The tested person is watching TV (Second session).
(Situation 21) Light is turned on (First session). N/A (Second session).
(Situation 22) The tested person is separated from others (First session). N/A (Second session).
(Situation 23) The tested person is in a lower area (First session). The tested person is in the middle (Second session).
(Situation 24) The tested person's length is 5.53 cm (First session). The tested person's length is 8.64cm (Second session).
(Situation 25) The tested person occupies an area of 9.45 $cm^2$ (First session). The tested person occupies an area of 24.37 $cm^2$ (Second session).
(Situation 26) There is a boundary between the father and the tested person (First session). The distance between the father and the tested person is 13.4 cm (Second session).
(Situation 27) There is a boundary between the mother and the tested person (First session). The distance between the mother and the tested person is 7.3 cm (Second session).
(Situation 28) There is a boundary between the brother and the tested person (First session). The distance between the brother and the tested person is 7.3 cm (Second session).
(Situation 29) There is a boundary between the father and the mother (First session). The distance between the father and the mother is 19.1 cm (Second session).
(Situation 30) There is a boundary between the father and the brother (First session). The distance between the father and the brother is 6.2 cm (Second session).
(Situation 31) There is a boundary between the mother and the brother (First session). The distance between the mother and the brother is 13.5 cm (Second session).
(Situation 32) The number of colors used in the drawing is 5 (First session). The number of colors used is 7 (Second session).
(Situation 33) The descending order of most frequently used colors are black, red, green, blue and yellow (First session). The descending order of most frequently used colors are blue, orange, black, yellow, red, green and purple (Second session).
(Situation 34) The areas of the colors are 36,265 pixels, 32,086 pixels, 24,896 pixels, 19,821 pixels and 14,341 pixels, respectively (First session). The areas of the colors are 255,792 pixels, 30,085 pixels, 26,338 pixels, 19,685 pixels, 8,780 pixels, 6,774 pixels and 4,279 pixels, respectively (Second session).
(Situation 35) The number of clusters is 41 (First session). The number of clusters is 37 (Second session).
(Situation 36) The completeness is 28.2% (First session). The completeness is 74.7% (Second session).
(Situation 37) The accuracy is 54.1% (First session). The accuracy is 78.6% (Second session).
(Situation 38) The concentration level is 22 percentile (First session). The concentration level is 2 percentile (Second session).

For example, if the Kinetic Family Drawings in FIGS. 2 and 3 are previous Kinetic Family Drawings and the Kinetic Family Drawings in FIGS. 7 and 8 are current Kinetic Family Drawings, the parsing module 301 evaluates the psychological state, symptoms or disorders of the person tested for art therapy, like those listed in Table 4, by using the personality information (INFO_C) and the art therapy knowledge (INFO_K) from the factor (ELM_2) analyzed from the current Kinetic Family Drawings.

TABLE 4

| Psychological state, symptoms or disorders | Assessment results, Art therapy knowledge (INFO_K) |
|---|---|
| (Interpretation 10) Family members have a good relationship with one another, and they communicate and collaborate with one another well. | (Situations 8, 9, 14, 17, 20 and 22), [Knowledge A3 and E9] |
| (Interpretation 11) The tested person has a peace of mind. | (Situation 38), [Knowledge P3] |
| (Interpretation 12) The brother has a more intimate relationship with the father than the tested person does. | (Situations 26 and 30), [Knowledge E5] |
| (Interpretation 13) The tested person has a more intimate relationship with the mother than the brother does. | (Situations 27 and 31), [Knowledge E5] |

Also, the parsing module 301 reads the evaluation information (INFO_E) of the previous Kinetic Family Drawings, like those of Table 5, from the database.

TABLE 5

| Psychological state, symptoms or disorders | Assessment results, Art therapy knowledge (INFO_K) |
|---|---|
| (Interpretation 1) The communication and relationship between the father and the tested person may be cut off. | (Situation 9), [Knowledge E3] |
| (Interpretation 2) The communication and relationship between the mother and the tested person may be cut off. | (Situation 14), [Knowledge E3] |
| (Interpretation 3) The communication and relationship between the father and the mother may be cut off. | (Situations 9 and 14), [Knowledge E3] |
| (Interpretation 4) The communication and relationship between the brother and the tested person may be cut off. | (Situation 22), [Knowledge E3] |
| (Interpretation 5) The tested person may be depressed or lack confidence, and may be in trauma and depression. | (Situations 22 and 33), [Knowledge C4 and E7] |
| (Interpretation 6) Father is the central figure in the family. | (Situation 10), [Knowledge E8] |
| (Interpretation 7) The tested person may have a negative attitude and repressive anger against the mother. | (Situation 10), [Knowledge E8] |
| (Interpretation 8) The father is respected or has authority. | (Situations 11 and 12), [Knowledge E4] |
| (Interpretation 9) The tested person is weary of everything. | (Situation 36), [Knowledge P1] |

Then, the parsing module 301 derives the changes of psychological state, symptoms or disorders, like those of Table 6, by comparing the evaluation information (INFO_E).

TABLE 6

| Changes in psychological state, symptoms or disorders | Recognition/Assessment results, Art therapy knowledge |
|---|---|
| (Interpretation 14) It can be inferred that the communication and relationship between the father and the tested person have been improved and that the family atmosphere has become better. | (Situations 8, 9, 20 and 22), [Knowledge A4 and E10] |
| (Interpretation 15) It can be inferred that the communication and relationship between the father and the brother have been improved and that the family atmosphere has become better. | (Situations 8, 9 and 17), [Knowledge A4 and E10] |
| (Interpretation 16) It can be inferred that the communication and relationship between the brother and the tested person have been improved. | (Situation 22), [Knowledge E10] |
| (Interpretation 17) The tested person has resolved the negative attitude and repressive anger at the mother and has begun to be positive about the mother. | (Situation 13), [Knowledge E11] |
| (Interpretation 18) The desire for love and affection has been mitigated. | (Situation 21), [Knowledge S3 and S6] |
| (Interpretation 19) The tested person is less depressed and thus has become more cheerful. | (Situation 32), [Knowledge C7] |
| (Interpretation 20) Trauma, depression and despair have been reduced. | (Situation 33), [Knowledge C4 and C10] |
| (Interpretation 21) The tested person has become less weary of everything. | (Situation 36), [Knowledge P4] |
| (Interpretation 22) This means symptoms of Attention Deficit Disorder have been relieved. | (Situation 37), [Knowledge P5] |
| (Interpretation 23) This means the tested person is emotionally more stable. | (Situation 38), [Knowledge P64] |

As such, a computer system and a computer-readable storage medium according to certain embodiments of the present invention can improve objectivity, consistency, reliability and validity while evaluating the psychological symptoms or disorders of a person tested for art therapy by using drawings, and can save an expert from the trouble of analyzing the drawings.

The above-described embodiments of the present invention can be written in a program executable by a computer and can be implemented in a general-purpose digital computer executing the program by using a computer-readable storage medium. The computer-readable storage medium includes a magnetic storage medium, for example, ROM, a floppy disk and a hard disk, an optically readable medium, for example, CD-ROM and DVD, and a carrier wave, for example, transmission over the Internet.

In the present invention, since drawing for art therapy, inputting, obtaining personality information of a client, analyzing, evaluating and parsing of a drawing and evaluating the psychological status of the client are automatically performed by a computer system, the objectivity, consistency, reliability and validity of an art therapy method can be improved, and the results thereof can be used as resources for the parents, teacher or art therapist of the client.

While the present invention has been described and illustrated with respect to particular embodiments, it shall be apparent to those skilled in the art that variations and modifications are possible without departing from the spirit and technical scope of the present invention. In one example, it is possible that an art therapy computer system and a method thereof according to an embodiment of the present invention can be implemented in a network-based server client system and telecommunication or an Internet-based mobile system. Thus, it shall be appreciated that the present invention is not restricted to the above embodiments and there can be a variety of embodiments within the technical scope of the present invention. As such, many embodiments other than those set forth above can be found in the appended claims, and such alternate embodiments are anticipated within the scope and spirit of the present invention.

The invention claimed is:

1. A computer system comprising:
a drawing module configured to present a plurality of patterns and to select a certain pattern and compose and color a drawing according to working of a person tested for art therapy;
an analysis module configured to analyze one or more factors from the colored drawing;
a parsing module configured to evaluate a psychological state, symptom or disorder of the person tested for art therapy from the analyzed factors; and
a database including a pattern library, in which the plurality of patterns are stored, drawing process information, which is about drawing processes of selecting the pattern and composing and coloring the drawing, and art therapy knowledge;
wherein the drawing module composes the drawing by performing at least one of placing the selected pattern, enlarging, reducing, rotating and deleting the entire or partial selected pattern and separating the patterns, in accordance with an operation by the person tested for art therapy.

2. The computer system of claim 1, wherein the drawing module independently performs vertical expansion, vertical reduction, horizontal expansion and horizontal reduction of each portion of the pattern.

3. The computer system of claim 1, wherein the drawing module provides a plurality of coloring tools in various thicknesses to the person tested for art therapy and performs coloring by using a coloring tool of a thickness selected by the person tested for art therapy.

4. The computer system of claim 1, wherein the drawing module provides the plurality of patterns stored in the pattern library to the person tested for art therapy.

5. The computer system of claim 1, wherein the analysis module analyzes a color-related factor by measuring at least one of the number of colors used in coloring the pattern, types of colors used in coloring the pattern, sequence of coloring, intensity of coloring, mixing of colors, color cluster, complementary colors, ratio of a primary color to a secondary color and ratio of a warm color to a cool color, from the colored drawing.

6. The computer system of claim 5, wherein the analysis module analyzes a performance-related factor by analyzing a completeness factor by measuring the number of pixels of a colored pattern and the number of pixels of the entire selected pattern, by analyzing an accuracy factor by measuring the degree of matching between clusters of the selected pattern and clusters of color, and then by analyzing a concentration factor by using a step regression analysis or standard regression analysis method of a multiple linear regression analysis in which the color-related factor, the completeness factor and the accuracy factor are explanatory variables.

7. The computer system of claim 1, wherein the analysis module analyzes a space-related factor including at least one of a length, size or width, rotation and separation of the selected pattern from the drawing and a distance, direction and the number of obstacles between the patterns.

8. The computer system of claim 7, wherein the analysis module measures a length or width of the selected pattern and a distance between the patterns by using pixels occupied by the selected pattern.

9. The computer system of claim 1, wherein the analysis module analyzes a form-related factor and a behavior-related factor by recognizing a form, type and behavior of the selected pattern.

10. The computer system of claim 1, wherein the parsing module evaluates psychological state, symptoms and disorders of the person tested for art therapy from the analyzed factors by using the database.

11. The computer system of claim 1, wherein the analysis module uses the drawing process information stored in the database to analyze the factors.

12. The computer system of claim 1, wherein the parsing module compares factors analyzed from a previously colored drawing and factors analyzed from a currently colored drawing by working of the person tested for art therapy and evaluates changes in the psychological state, symptoms or disorders by using art therapy knowledge in which comparison results of the factors are matched against the changes of the psychological state, symptoms or disorders.

13. The computer system of claim 1, wherein the parsing module evaluates changes in the psychological state, symptoms or disorders by comparing a result evaluated from a previously colored drawing and a result evaluated from a currently colored drawing by working of the person tested for art therapy.

14. The computer system of claim 1, wherein the database further comprises personality information of the person tested for art therapy.

15. The computer system of claim 14, further comprising a personality information obtaining unit configured to obtain the personality information from the person tested for art therapy through a survey and store the obtained personality information in the database.

16. A non-transitory computer readable storage medium having a computer executable recorded program:
providing a plurality of patterns to a person tested for art therapy;
drawing a picture by selecting, composing and coloring a certain pattern according to working of the person tested for art therapy;
analyzing a plurality of factors from the picture; and
evaluating psychological state, symptoms or disorders of the person tested for art therapy by using art therapy knowledge in which the plurality of factors are matched against the psychological state, symptoms or disorders;
wherein the drawing, a picture is performed by the drawing module which composes the drawing by performing at least one of placing the selected pattern, enlarging, reducing, rotating and deleting the entire or partial selected pattern and separating the patterns, in accordance with an operation by the person tested for art therapy.

17. An art therapy method comprising:
providing a plurality of patterns to a person tested for art therapy;
drawing a picture by selecting, composing and coloring a certain pattern according to working of the person tested for art therapy;
analyzing a plurality of factors from the picture; and
evaluating psychological state, symptoms or disorders of the person tested for art therapy by using art therapy knowledge in which the plurality of factors are matched against the psychological state, symptoms or disorders;
wherein the drawing a picture is performed by the drawing module which composes the drawing by performing at least one of placing the selected pattern, enlarging, reducing, rotating and deleting the entire or partial selected pattern and separating the patterns, in accordance with an operation by the person tested for art therapy.

18. The method of claim 17, further comprising being provided with personality information from the person tested for art therapy,
wherein, the evaluating of the psychological state, symptoms or disorders is performed by evaluating the psychological state, symptoms or disorders of the person tested for art therapy by additionally using the personality information.

19. The method of claim 18, further comprising evaluating changes in psychological state, symptoms or disorders of the person tested for art therapy by comparing a previously drawn picture and a currently drawn picture according to working of the person tested for art therapy.

* * * * *